United States Patent [19]

Nonomura

[11] Patent Number: 5,163,842
[45] Date of Patent: Nov. 17, 1992

[54] PROCESS AND APPARATUS FOR PRODUCING DENTAL FILLING FOR RESTORATION OF TOOTH CROWN

[76] Inventor: Yuusuke Nonomura, 54, Nishizato-cho 2-chome, Meitou-ku, Nagoya-shi, Aichi-ken, Japan

[21] Appl. No.: 846,711

[22] Filed: Mar. 6, 1992

[30] Foreign Application Priority Data

Mar. 12, 1991 [JP] Japan .................................. 3-74033

[51] Int. Cl.⁵ .............................................. A61C 3/00
[52] U.S. Cl. ........................................ 433/75; 433/76; 433/114; 433/226
[58] Field of Search .................. 433/75, 76, 114, 215, 433/223, 226

[56] References Cited

U.S. PATENT DOCUMENTS

| | | | |
|---|---|---|---|
| 3,218,624 | 11/1965 | Zane | 433/76 |
| 3,861,044 | 1/1975 | Swinson, Jr. | 433/226 |
| 4,182,312 | 1/1980 | Mushabac | 433/68 |
| 4,411,626 | 10/1983 | Becker et al. | 433/223 |
| 4,478,580 | 11/1984 | Barrut | 433/223 |
| 4,575,805 | 3/1986 | Moermann et al. | 433/223 |
| 4,837,732 | 6/1989 | Brandestini et al. | 433/223 |
| 4,937,928 | 7/1990 | van der Zel | 433/223 |
| 4,941,826 | 7/1990 | Loran et al. | 433/76 |
| 5,017,139 | 5/1991 | Mushabac | 433/76 |

OTHER PUBLICATIONS

CAD/CAM Systems In Dentistry-A System for Automated Fabrication of Dental Prostheses, E. Dianne Rekow, Feb.-Mar. 1987, pp. 1-14.

Primary Examiner—John J. Wilson
Attorney, Agent, or Firm—Parkhurst, Wendel & Rossi

[57] ABSTRACT

Process and apparatus for producing a dental filling for restoration of a tooth crown, the dental filling being fitted to a cavity prepared in the tooth for filling the cavity. The apparatus includes a cutting device for preparing the cavity, the cutting device including a cutting element for cutting the tooth for the cavity preparation, and a cutting-element position sensor for monitoring movement of the cutting element for the cavity preparation and thereby producing a batch of outline form data representing a three-dimensional outline form of the cavity; a memory device for storing the batch of outline form data; a machining device for machining a prefabricated filling blank into the dental filling; and a control device for controlling operation of the machining device according to the batch of outline form data, so that the filling blank is machined into the dental filling having an outline form identical with the outline form of the cavity.

10 Claims, 6 Drawing Sheets

PROCESS AND APPARATUS FOR PRODUCING DENTAL FILLING FOR RESTORATION OF TOOTH CROWN

BACKGROUND OF THE INVENTION

1. Field of the Invention

The present invention generally relates to a process and an apparatus for producing a dental filling for restoration of a tooth crown, and particularly to the technique of producing such a dental filling with ease and with high form accuracy.

2. Related Art Statement

As one of known dental restoration techniques of repairing or filling a damage of hard tissue of a tooth crown and thereby restoring the function of the tooth, there is the technique of preparing a cavity in the tooth crown by cutting and grinding the damaged hard tissue and then fitting to the cavity a solid, dental filling (e.g., inlay, onlay, core, crown, bridge) which has been produced to have an external shape or form corresponding to the cavity.

A dental filling for restoration of a tooth crown is formed of metal, porcelain, composite resin, etc. In particular, metal and porcelain are preferable filling materials, because those materials have high strength and high abrasion resistance. Whichever material is selected, an impression (i.e., imprint of a tooth) is taken from a tooth in which a cavity has been prepared, and a model (i.e., replica of the tooth) is formed of, for example, plaster on the impression. This model is used for producing a dental filling to be fitted to the cavity, in a manner suitable for the selected material.

More specifically, in the event that metal is selected as filling material, it is a common practice that a model is used for forming a wax pattern corresponding to a tooth including a cavity; the wax pattern is immersed in a fireproof investment such as plaster; the plaster is heated for removing or evaporating the wax pattern and thereby obtaining a mold; the mold is used for casting the metal; and the cast metal is cut, ground and polished into a final, dental filling. Meanwhile, in the event that porcelain is selected, it is common that a model is used for producing a secondary model; wet porcelain mix is applied to the cavity of the secondary model, and then they are fired; the fired porcelain is cut, ground and polished into a final dental filling.

However, any of the known techniques in which various sorts of materials are used for producing a dental filling, essentially requires taking an impression of a tooth, forming a model on the impression, and producing a pattern or a secondary model using the model. Thus, those techniques are very cumbersome to carry out, need a long time, and cost high.

In addition, since, in the conventional dental filling production techniques, information representing the external shape or form of a tooth having a cavity, is transmitted to a final dental filling via a plurality of intermediates such as a model, pattern, or secondary model, dimensional errors accumulate because of deformation, shrinkage, and/or expansion of the materials of those intermediates. Thus, it has been very difficult to produce a dental filling with desired dimensional accuracy. Accordingly, a skillful technician is needed for the dental filling production. However, recently, dental technicians have been short in number, even posing a social problem.

Furthermore, while attention has been directed to using porcelain as a filling material because of its excellent color tone and gloss, high corrosion resistance, and high mechanical strength, a satisfactory technique of producing a dental filling using porcelain has not been established yet. The reasons for that are as follows: It is very difficult to control firing of porcelain under high temperature and high pressure. Although porcelain shrinks, i.e., reduces in volume, more than several tens percent due to the firing, it is very difficult to take into account, in advance, the amount of shrinkage of the porcelain, unlike industrial products. In addition, dental fillings are required to have different external forms corresponding to individual teeth. Thus, no conventional technique can provide a porcelain dental filling with desired qualities, in particular, mechanical strength, at low cost.

SUMMARY OF THE INVENTION

In the above-described background, the present invention has been developed. It is therefore an object of the present invention to provide a process and an apparatus for producing a dental filling for restoration of a tooth crown, with ease and with high dimensional accuracy, thereby reducing to practice a high-quality, porcelain dental filling, for example, which has been difficult to produce by the conventional techniques.

The above object has been achieved by the present invention. According to a first aspect of the present invention, there is provided a process of producing a dental filling for restoration of a tooth crown, the dental filling being fitted to a cavity prepared in the tooth for filling the cavity, comprising the steps of (1) monitoring, using a cutting-element position sensor, movement of a cutting element for preparing the cavity, and thereby producing a batch of outline form data representing a three-dimensional outline form of the cavity, and (2) machining a prefabricated filling blank according to the batch of outline form data, into the dental filling having an outline form identical with the outline form of the cavity.

In the dental filling production process arranged as described above, the three-dimensional outline form of a cavity prepared in a tooth by cutting and grinding thereof, is transformed into a batch of outline form data, simultaneously with the preparation of the cavity. The batch of outline data is used directly for machining a prefabricated filling blank into a dental filling, so that the dental filling has an outline form identical with the outline form of the cavity. Thus, the present process does not require cumbersome steps such as taking an impression of a tooth or forming a model of the same. That is, the present process ensures that a desired dental filling is produced with ease and in a short time.

In the present process, it is possible to produce a dental filling by machining a pre-cast or pre-fired filling material. Thus, it is not required to take into account the amount of deformation and/or shrinkage of the filling material due to, for example, firing thereof. Therefore, in the present process, some materials which have conventionally been difficult to use can be used, without difficulty, as a filling material. Thus, the present process provides dental fillings with higher qualities offered by those materials.

According to a second aspect of the present invention, there is provided an apparatus for producing a dental filling for restoration of a tooth crown, the dental filling being fitted to a cavity prepared in the tooth for filling the cavity, comprising (a) cutting means for preparing the cavity, the cutting means including a cutting element for cutting the tooth for the cavity preparation, and a cutting-element position sensor means for monitoring movement of the cutting element for the cavity preparation and thereby producing a batch of outline form data representing a three-dimensional outline form of the cavity, (b) memory means for storing the batch of outline form data, (c) machining means for machining a prefabricated filling blank into the dental filling, and (d) control means for controlling operation of the machining means according to the batch of outline form data, so that the filling blank is machined into the dental filling having an outline form identical with the outline form of the cavity.

In a preferred embodiment in accordance with the second aspect of the invention, the cutting means further includes an immobilizing means for immobilizing the tooth.

In another embodiment in accordance with the second aspect of the invention, the cutting means further includes a tooth position sensor means for monitoring displacement of the tooth and thereby producing a batch of displacement data representing the displacement of the tooth, and an adjusting means for adjusting the batch of outline form data based on the batch of displacement data.

Since the outline form of the cavity prepared in the tooth is more accurately detected by the cutting-element position sensor means because of employment of the immobilizing means, or of the tooth-position sensor means and adjusting means, the present apparatus is more advantageous for producing a dental filling with metal or porcelain which requires a strict similarity between the outline forms of the cavity and the filling.

BRIEF DESCRIPTION OF THE DRAWINGS

The above and optional objects, features and advantages of the present invention will be better understood by reading the following detailed description of the presently preferred embodiments of the invention when considered in conjunction with the accompanying drawings, in which.

DETAILED DESCRIPTION OF THE PREFERRED EMBODIMENTS

Figure 1:
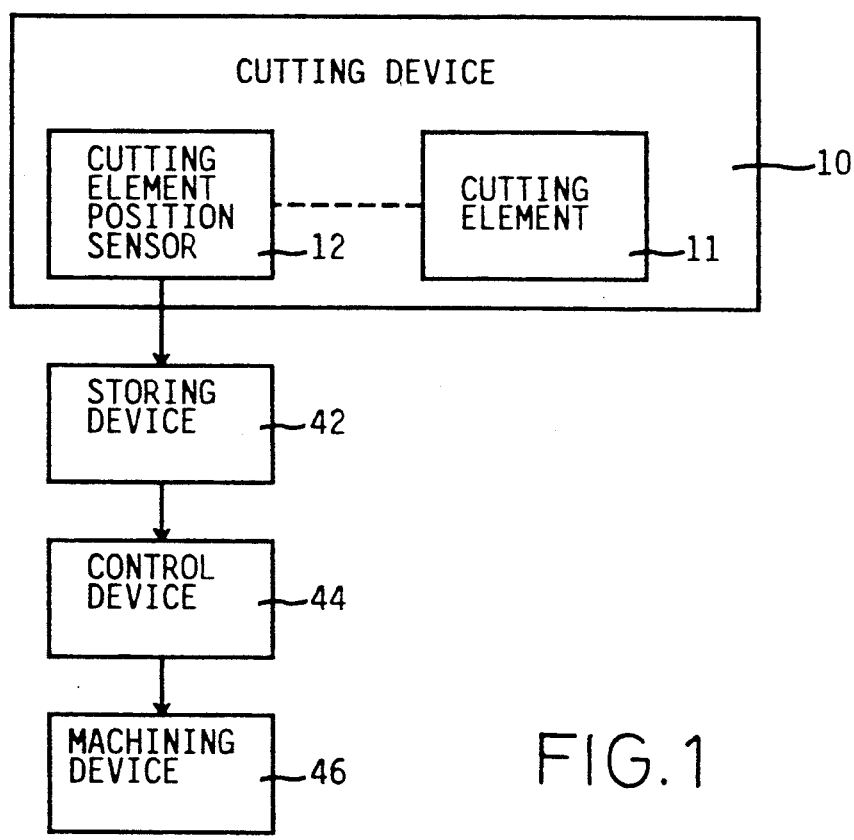
FIG. 1 is a diagrammatic view of a dental filling production system embodying the present invention.

Referring first to FIG. 1, there is shown a production system in accordance with the present invention, for producing a dental filling for restoration of a tooth crown. In the figure, reference numeral 10 designates a dental cutting device which, as well known, includes a power drive such as an electric engine and a cutting element 11 secured to a handpiece (28, FIG. 2) operatively connected to the power drive. The cutting element 11 is rotated at high speed by the power drive, for cutting and grinding a tooth. The cutting device 10 further includes a cutting-element position sensor 12 for detecting three-dimensional movement of the cutting element 11. When the cutting element 11 is moved for cutting the tooth and thereby preparing a cavity in the tooth crown, the position sensor 12 monitors the movement of the cutting element 11, and produces a batch of outline form data representing a three-dimensional outline form of the cavity prepared. The present system utilizes the batch of outline form data for producing a dental filling to be fitted to the cavity prepared in the tooth crown.

The cutting-element position sensor 12 employed in the cutting device 10 may be constituted by one of various sorts of sensors; such as an electric sensor, optical sensor, or magnetic sensor. Two examples of the position sensor 12 are shown in FIGS. 2 and 3, respectively.

Figure 2:
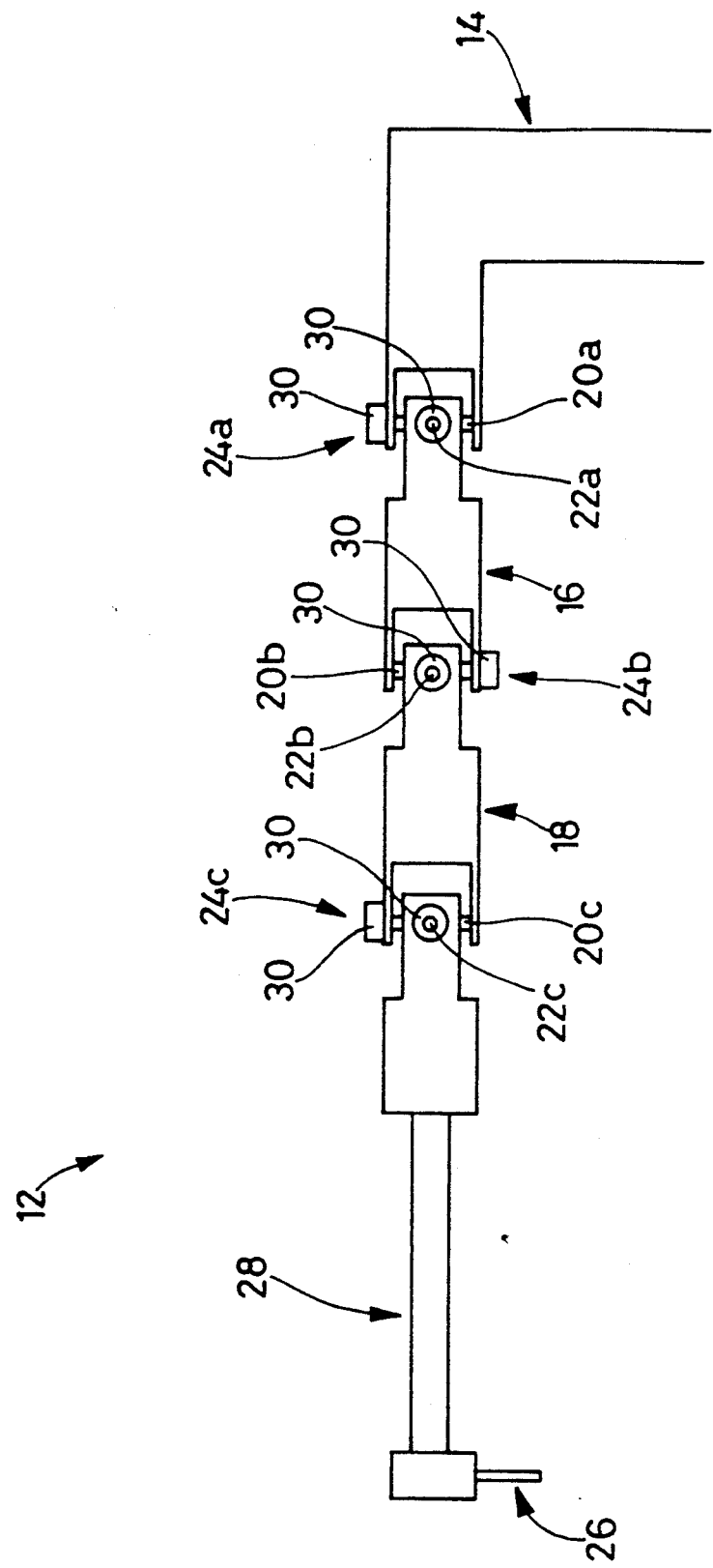
FIG. 2 is an illustrative view of a cutting-element position sensor employed in the system of FIG. 1.
Figure 3:
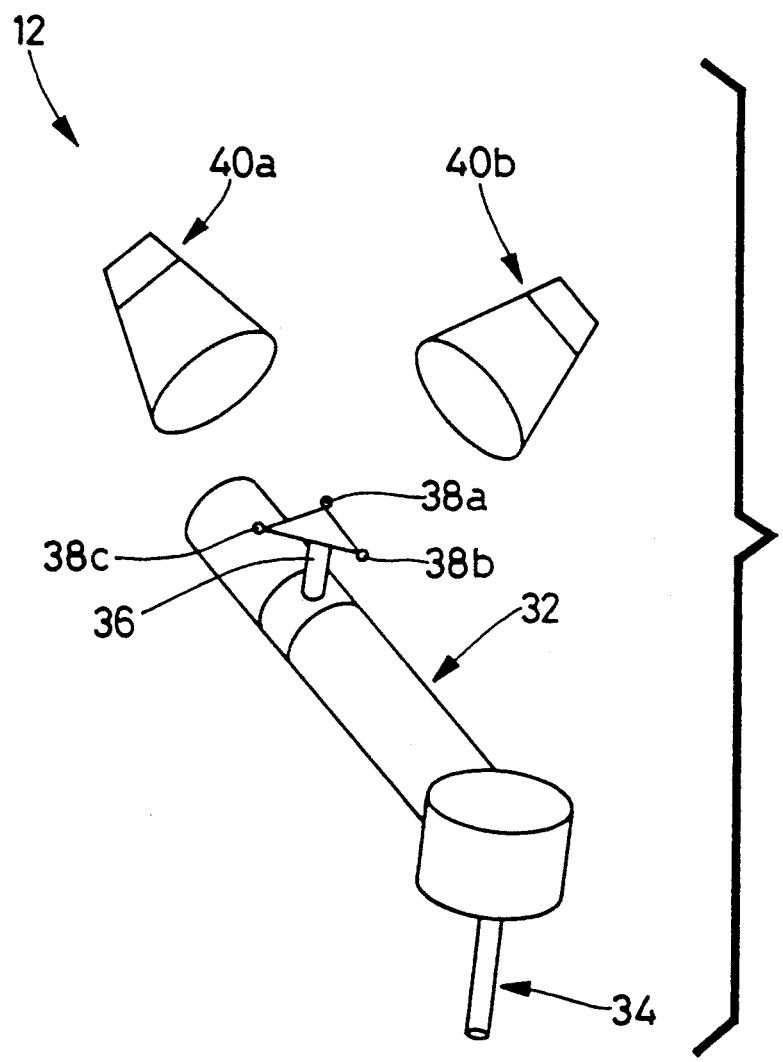
FIG. 3 is an illustrative view of another cutting-element position sensor employed in the system of FIG. 1.

First, in FIG. 2, there is shown an electric position sensor 12. In the figure, reference numeral 14 denotes a stationary support member of a fixed main body (not shown) of the cutting device 10. A first and a second arm member 16, 18 are connected to the support member 14 in series via a first and a second universal joint 24a, 24b. Each universal joint 24a, 24b has two pivot axes 20a and 22a, or 20b and 22b, perpendicular to each other. In addition, a handpiece 28 is connected to the second arm member 18 in series via a third universal joint 24c having two pivot axes 20c, 22c perpendicular to each other. A cutting element 26 is detachably attached to a free end of the handpiece 28. Since the handpiece 28 is supported by the stationary support member 14 of the cutting device 10 via the three universal joints 24a, 24b, 24c, the cutting element 26 is freely movable or pivotable with respect to the six axes 20a, 22a, 20b, 22b, 20c, 22c.

FIG. 2 shows the first and second arm members 16, 18 and handpiece 28 being extended completely. When the cutting element 26 is actually operated, those members 16, 18, 28 will be pivoted about the individual universal joints 24a, 24b, 24c, so as to permit the handpiece 28 or cutting element 26 to freely be moved. The first and second arm members 16, 18 and handpiece 28 may resiliently be connected to each other, or to the support member 14 of the cutting device 10, as needed, so as to improve the operability of the handpiece 28.

The electric position sensor 12 of FIG. 2 further includes a rotary encoder 30 for each of the six pivot axes 20a, 22a, 20b, 22b, 20c, 22c of the first to third universal joints 24a, 24b, 24c. Each of the six rotary encoders 30 produces an electric signal, such as a pulse signal, representing an amount of rotation of a corresponding one of the six pivot axes 20a, 22a, 20b, 22b, 20c, 22c.

When the handpiece 28, or the cutting element 26 secured to the handpiece 28, is moved for cutting the tooth, the six rotary encoders 30 produce six electric signals which cooperate with each other to represent the three-dimensional movement of the cutting element 26.

Meanwhile, FIG. 3 shows an optical position sensor 12 for detecting movement of a cutting element 34. In the figure, reference numeral 32 designates a handpiece to which the cutting element 34 is secured. The handpiece 32 may flexibly be connected to a stationary member (e.g., member 14 in FIG. 2) of the cutting device 10 in the same manner as that shown in FIG. 2, or may be constituted as an independent member in which a small-size motor ("micromotor") is incorporated and which is structurally independent of the other elements. The handpiece 32 includes a shank and a support bar 36 protruding from the shank. The support bar 36 supports three point light sources 38a, 38b, 38c which are spaced apart from each other in a common plane. The point light sources 38a, 38b, 38c may be constituted by light emitting diodes (LED), or optical fibers.

The optical position sensor 12 further includes a stereoscopic image pick-up element such as a pair of coupled device (CCD) cameras 40a, 40b or PSD (positioning sensitive device) cameras spaced apart from each other. The CCD cameras 40a, 40b are fixed to, or supported by, a support frame (not shown) at those positions which permit the CCD cameras 40a, 40b to sufficiently cover the space in which the three point light sources 38a, 38b, 38c are moved around when the handpiece 32 is used for cutting the tooth.

When the handpiece 32, or the cutting element 34 secured to the handpiece 32, is moved for cutting the tooth, the movement thereof is determined by detecting the movement of the three point light sources 38a, 38b, 38c through the CCD cameras 40a, 40b, and is transformed into an electric signal.

As shown in FIG. 1, the present production system further includes a storing device 42 for storing the position signal supplied from the cutting-element position sensor 12. The position signal represents the three-dimensional movement of the cutting element 11 for preparing a cavity in a tooth crown by cutting and grinding thereof, and therefore serves as a batch of outline form data representing a three-dimensional outline form of the cavity prepared in the tooth crown.

Since, strictly, the electric or optical position sensor 12 shown in FIG. 2 or FIG. 3 detects the movement of not the cutting element 26, 34 but the handpiece 28, 32, the position signal supplied from the position sensor 12 is adjusted, as needed, depending on the configuration or external shape of the cutting element 26, 34 secured to the handpiece 28, 32.

The position signal produced from the cutting-element position sensor 12 and stored in the storing device 42 is transferred to a control device 44 after the cavity preparation has been completed. The control device 44 controls operation of a machining device 46, so that the machining device 46 machines a prefabricated blank into a dental filling according to the position signal, which thus serves as machining information.

More specifically, the machining device 56 may be selected from various sorts of known machining apparatus such as grinding machine, electric discharge machine, laser beam machine, depending on the selected sort of material for the dental filling. Since the position signal provided by the cutting-element position sensor 12 is directly used by the control device 44 for controlling the machining operation of the machining device 46, the machining device 46 machines the prefabricated filling blank into the dental filling, so that the dental filling machined has a three-dimensional outline form identical with that of the cavity prepared in the tooth crown.

It is possible to machine out an occlusal surface (i.e., top surface) of the dental filling by using an impression which has been taken from the occlusal surface of the tooth before the cavity is prepared. Alternatively, however, it is possible that, before the cavity preparation, the external shape of the tooth is detected and transformed into position data by utilizing the position sensor 12, specifically, tracing the external shape of the tooth with the cutting element 11. The position signal may be stored in the storing device 42, and further be used when the prefabricated material is machined into the dental filling, or when the dental filling is finished for the occlusion adjustment for fitting to the tooth cavity.

As emerges from the foregoing description, the present dental filling production system easily obtains information on the external shape of a dental filling to be fitted to a cavity prepared in a tooth crown, when the cavity is prepared. In addition, the production system directly uses the obtained information for machining a prefabricated filling material into the dental filling, so that the dental filling has an external shape identical with that of the cavity prepared in the tooth. Thus, the present production system produces the dental filling without needing cumbersome steps such as taking an impression or forming a model.

The present production system provides a dental filling for restoration of a tooth crown, with much ease and in a short time. The operation of the present production system does not require great skill. Therefore, the present system easily produces a dental filling with high quality.

In addition, since the present production system produces a dental filling by machining a prefabricated material (filling material) according to the stored data, the present system does not require cumbersome steps, such as casting or firing, which have conventionally been necessary for producing an individual dental filling. Furthermore, the present system is free from the problem of taking into account the shrinkage amount of a filling material due to firing thereof. Therefore, the present system is advantageously applicable to the production of a dental filling using some sorts of materials which have been difficult to use in the known techniques. Thus, the present system easily provides a dental filling with high quality offered by such a material.

Figure 4:
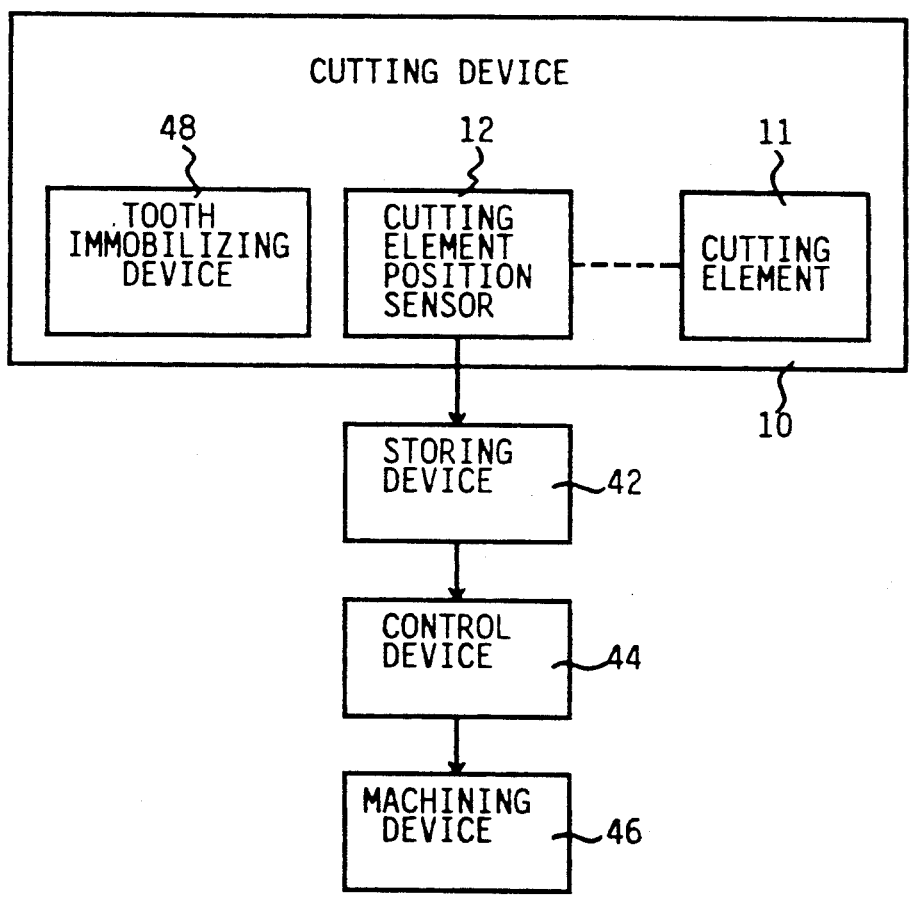
FIG. 4 is a diagrammatic view of another embodiment of the dental filling production system of the present invention.

Referring next to FIG. 4, there is shown another embodiment according to the present invention, for producing a dental filling for restoration of a tooth crown. The same reference numerals as used in FIG. 1 are used for designating corresponding parts or elements of the instant embodiment, and the description of those parts or elements are omitted.

The instant production system has a cutting device 10 including a handpiece (not shown) to which a cutting element 11 is detachably attached, and a cutting-element position sensor 12 for monitoring movement of the cutting element 11. The cutting device 10 further includes a fitting member 48 for immobilizing a tooth to be cut, relative to a stationary member (e.g., member 14 in FIG. 2) of the cutting device 10, so as to prevent the tooth from moving around.

Figure 5:
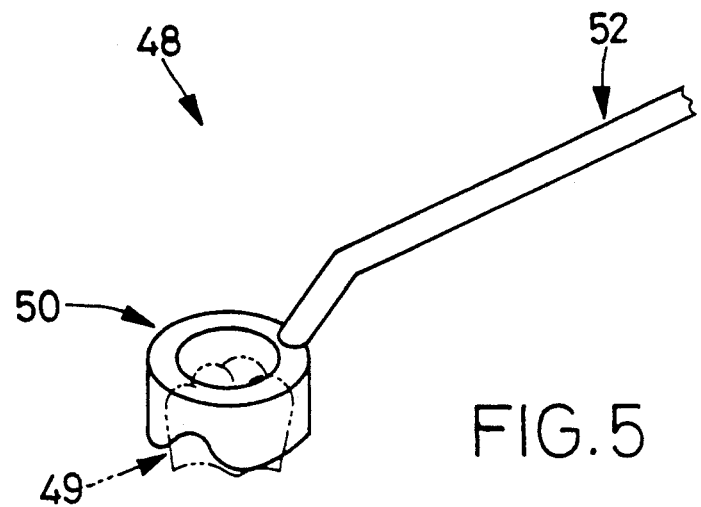
FIG. 5 is a perspective view of a tooth immobilizing device employed in the system of FIG. 4.

More specifically, the fitting member 48 includes, as shown in FIG. 5, a fitting portion 50 to be fitted on a tooth 49 such as a damaged tooth of a patient, and a rod portion 52 extending from the fitting portion 50. With the fitting portion 50 being fitted on the tooth 49, the rod portion 52 extends out of the mouth of the patient, so that the rod portion 52 is fixed relative to the stationary member of the cutting device 10.

The fitting portion 50 of the fitting member 48 may be constituted and used such that an element having a configuration generally corresponding to a normal tooth configuration is fitted on side surfaces of the tooth 49 by fastening a thread fastener, or by using an appropriate adhesive. Alternatively, it is possible to take an impression of the tooth 49 and produce an element having a configuration corresponding to that of the tooth 49, so that the produced element is fitted on the tooth 49. Furthermore, the fitting portion 50 may be constituted for fitting on a plurality of teeth of the patient.

The instant dental filling production system prevents a tooth from displacing, when the tooth is cut to prepare a cavity in the tooth. Thus, the present system effectively prevents the cutting element position sensor 12 from producing position signal including errors caused by the displacement of the tooth.

Therefore, the instant production system detects, with high accuracy, a three-dimensional outline form of a cavity even in the even that the cavity is prepared over a long period of time. In addition, since a dental filling is produced by a machining device 46 by using the accurate outline form of the cavity, the dental filling produced enjoys improved accuracy of the outline form thereof.

The first embodiment of FIG. 1 which does not have an immobilizing member like the fitting member 48 of FIG. 5, is preferably used, for example, for producing a resin filling, or a center post of a core to be fitted in an internal cavity. The resin filling and the core's center post are not required to have high dimensional accuracy. Meanwhile, the second embodiment of FIG. 4 which has the immobilizing member 48 is preferably used for producing a dental filling such as a metal or porcelain inlay that requires high dimensional accuracy.

Figure 6:
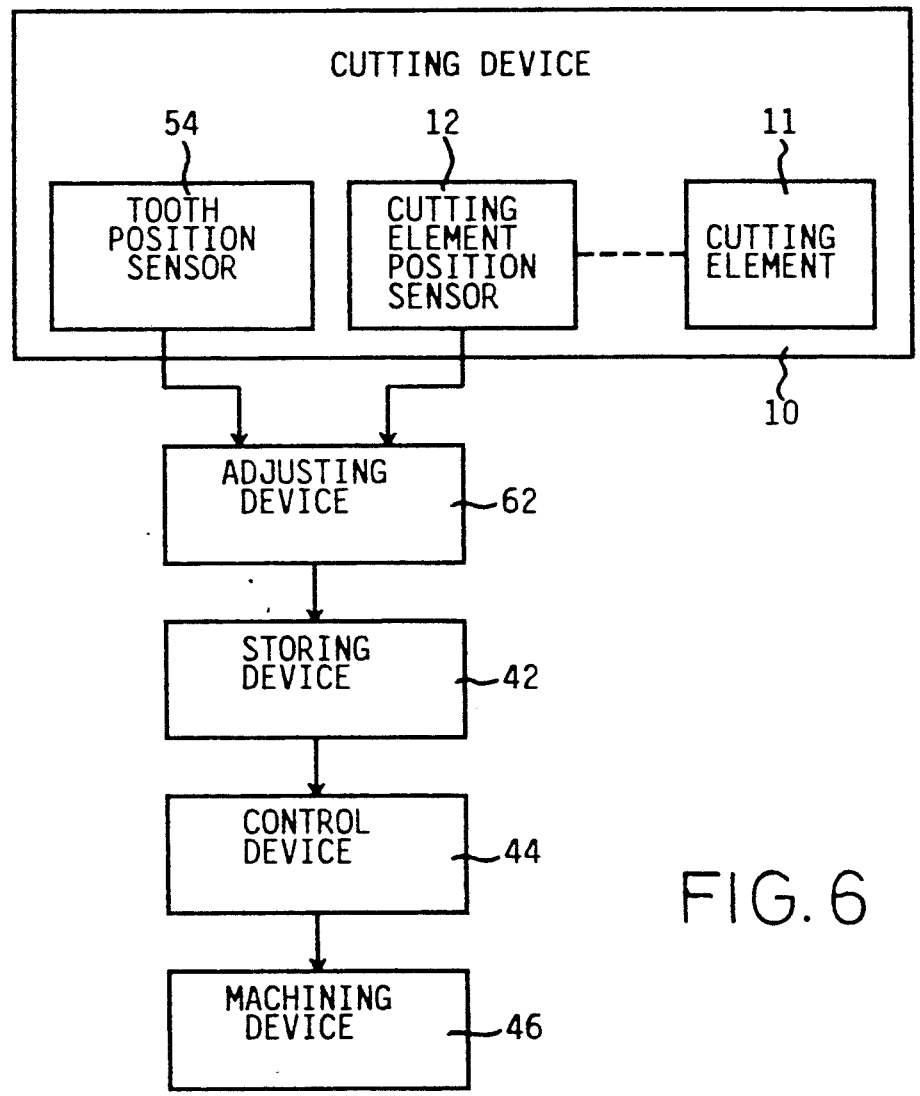
FIG. 6 is a diagrammatic view of yet another embodiment of the dental filling production system of the present invention.

Referring further to FIG. 6, there is shown a third embodiment in accordance with the present invention, for producing a dental filling for restoration of a tooth crown. The same reference numerals as used in FIG. 1 are used for designating corresponding parts or elements of the instant embodiment, and the description of those parts or elements are omitted.

The present production system has a cutting device 10 which includes a handpiece (not shown) to which a cutting element 11 is detachably attached, and a cutting-element position sensor 12 for monitoring movement of the cutting element 11. The cutting device 10 further includes a tooth position sensor 54 for monitoring displacement of a tooth 55 caused by motion of patient's body, while the tooth 55 is cut and ground by the cutting element 11.

Figure 7:
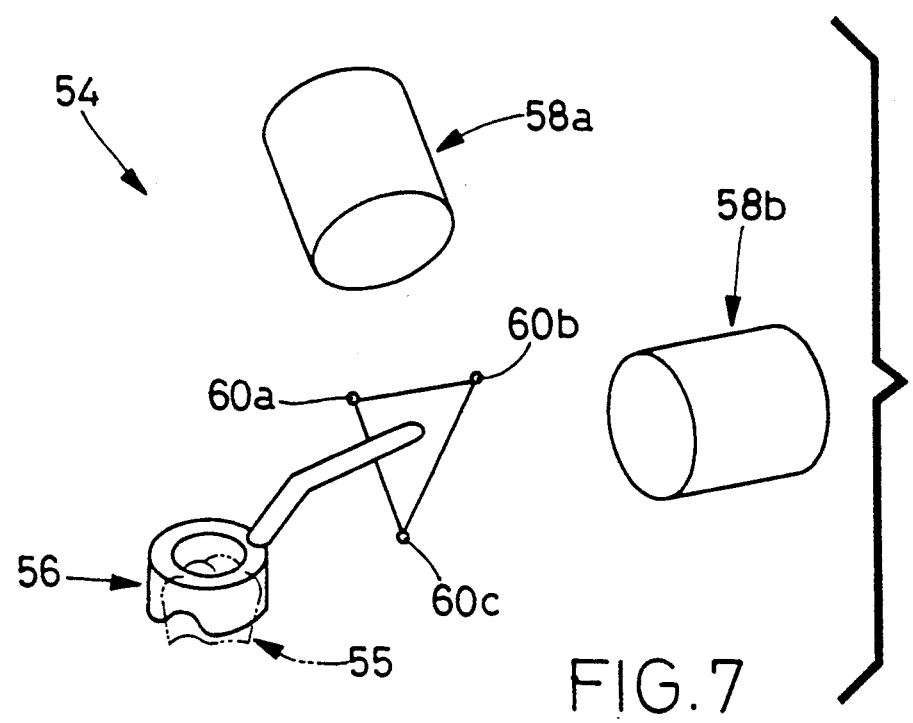
FIG. 7 is an illustrative view of a tooth-position sensor employed in the system of FIG. 6.

More specifically, the tooth position sensor 54 may be constituted by, for example, an optical sensor device as shown in FIG. 7. The optical sensor device 54 includes a fitting member 56 to be fitted to the tooth 55 and three point light sources 60a, 60b, 60c fixed to the fitting member 56. The point light sources 60a, 60b, 60c may be light emitting diodes (LED) or optical fibers. The sensor device 54 further includes a stereoscopic image pick-up element in the form of a pair of charge-coupled device (CCD) cameras 58a, 58b or PSC (positioning sensitive device) cameras spaced apart from each other. The CCD cameras 58a, 58b are fixed to, or supported by, a stationary member (not shown) of the cutting device 10, at those positions which permit the CCD cameras 58a, 58b to sufficiently cover the space in which the light sources 60a, 60b, 60c are moved. The tooth position sensor 54 monitors the displacement of the tooth 55 by detecting the movement of the light sources 60a, 60b, 60c, and produces an electric signal.

The electric signal provides a batch of displacement data representing the three-dimensional displacement of the tooth 55.

The tooth position sensor 54 may be constituted by an electric sensor which includes a fitting member to be fitted to a tooth and a connection mechanism, as shown in FIG. 2, for connecting the fitting member to the stationary member of the cutting device 10. In this case, the amount of displacement (i.e., rotation) with respect to each of the six axes of the connecting mechanism may be detected by a potentiometer associated with the each axis. Alternatively, the tooth position sensor 54 may be constituted by a magnetic sensor.

In the case where the tooth position sensor 54 is not adapted to detect the relative position of the tooth 55 relative to the position of the cutting element 11 detected by the cutting-element position sensor 12, it is required to establish the positional relationship between the tooth 55 (or fitting member 56) and the cutting element 11, for example by flexibly connecting the cutting element 11 to the fitting member 56 through a pin, groove, or hole.

The displacement signal produced by the tooth position sensor 54, which signal is representative of the displacement of the tooth 55, is supplied to an adjusting device 62. The adjusting device 62 adjusts or corrects the position signal from the cutting-element position sensor 12, according to the displacement signal from the tooth position sensor 54, by removing from the position signal the errors caused by the displacement of the tooth 55.

Like the second embodiment of FIG. 4, the present production system detects with higher dimensional accuracy the three-dimensional outline form of the cavity prepared using the cutting element 11, and thereby produces a dental filling to be fitted to the cavity, with improved form or shape accuracy.

In addition, the present system does not require that the tooth 55 be immobilized when the tooth 55 is being cut and ground. Therefore, the cavity preparation is easily carried out, and the patient does not feel discomfort due to such immobility.

While the present invention has been described in its presently preferred embodiments, it is to be understood that the present invention is by no means limited to the details of those embodiments but may otherwise be embodied.

For example, the construction or arrangement of the cutting-element position sensor 12 or tooth position sensor 54 is not limited to the particulars of the illustrated embodiments. Specifically, one or more of the six axes 20a, 22a, 20b, 22b, 20c, 22c of the connecting mechanism for connecting the handpiece 28 to the stationary member 14 of the cutting device 10, shown in FIG. 2, may be replaced by one or more linearly movable elements. In this case, the amount of linear movement may be detected by a linear encoder.

Furthermore, the optical position sensor 12, 54 shown in FIG. 3 or FIG. 7 may be so constructed as to have four or more point light sources, or have three or more image pick-up elements, for improving the accuracy of detection.

In the third embodiment of FIG. 6, the position signal corrected by the adjusting device 62 is supplied to the storing device 42. However, the production system may be adapted such that the storing device 42 stores both the position signal from the cutting-element position sensor 12 and the displacement signal from the tooth position sensor 54, and the control device 44 adjusts the position signal based on the displacement signal. In this case, the control device 44 serves as adjusting means.

It is to be understood that the present invention may be embodied with other changes, improvements and modifications that may occur to those skilled in the art without departing from the scope and spirit of the invention defined in the appended claims.

What is claimed is:

1. A process of producing a dental filling for restoration of a tooth crown, the dental filling being fitted to a cavity prepared in the tooth for filling the cavity, comprising the steps of:

monitoring, using a cutting-element position sensor, movement of a cutting element for preparing said cavity, and thereby producing a batch of outline form data representing a three-dimensional outline form of said cavity, and machining a prefabricated filling blank according to said batch of outline form data, into said dental filling having an outline form identical with the outline form of said cavity.

2. An apparatus for producing a dental filling for restoration of a tooth crown, the dental filling being fitted to a cavity prepared in the tooth for filling the cavity, comprising:

cutting means for preparing said cavity,
said cutting means including a cutting element for cutting the tooth for the cavity preparation, and a cutting-element position sensor means for monitoring movement of said cutting element for said cavity preparation and thereby producing a batch of outline form data representing a three-dimensional outline form of said cavity;

memory means for storing said batch of outline form data;

machining means for machining a prefabricated filling blank into said dental filling; and control means for controlling operation of said machining means according to said batch of outline form data, so that said filling blank is machined into said dental filling having an outline form identical with the outline form of said cavity.

3. An apparatus according to claim 2, wherein said cutting means further includes an immobilizing means for immobilizing said tooth.

4. An apparatus according to claim 3, wherein said immobilizing means includes a fitting member having a fitting portion adapted to be fitted on said tooth, and a rod portion extending from said fitting portion, said rod portion being stationary relative to a reference position.

5. An apparatus according to claim 2, wherein said cutting means further includes:

a tooth position sensor means for monitoring displacement of said tooth and thereby producing a batch of displacement data representing the displacement of said tooth; and an adjusting means for adjusting said batch of outline form data based on said batch of displacement data.

6. An apparatus according to claim 5, wherein said tooth position sensor means includes:

a fitting member having a fitting portion adapted to be fitted on said tooth, and a rod portion extending from said fitting portion;

three point light sources which are supported by said rod portion of said fitting member such that the light sources are stationary relative to said fitting portion; and a stereoscopic image pick-up means for continuously taking a stereoscopic image of said three point light sources when the light sources are displaced with said tooth during said cavity preparation, said stereoscopic image continuously taken by said image pick-up means providing said batch of displacement data.

7. An apparatus according to claim 2, wherein said cutting means further includes:

a stationary support member;
at least one arm member;
a handpiece to which said cutting element is attached; and
a plurality of universal joints connecting said stationary support member, said at least one arm member, and said handpiece in series, and thereby connecting said cutting element to said stationary support member.

8. An apparatus according to claim 7, wherein each of said universal joints has a pair of pivot axes perpendicular to each other, said cutting-element position sensor means including a rotary encoder associated with each of said pivot axes, for detecting a rotation amount of a corresponding one of said handpiece and said at least one arm member about said each pivot axis, said rotary encoder generating an electric signal representing the detected rotation amount, the electric signals generated by the rotary encoders associated with the pivot axes of said universal joints cooperating with each other to provide said batch of outline form data.

9. An apparatus according to claim 2, wherein said cutting means further includes a handpiece to which said cutting element is attached, said cutting-element position sensor means including:
three point light sources which are supported by said handpiece such that the light sources are stationary relative to said cutting element; and
a stereoscopic image pick-up means for continuously taking a stereoscopic image of said three point light sources when the light sources are moved with said cutting element for said cavity preparation, said stereoscopic image continuously taken by said image pick-up means providing said batch of outline form data.

10. An apparatus according to claim 9, wherein said stereoscopic image pick-up means includes a pair of charge-coupled device cameras.

* * * * *